United States Patent [19]
Eskamani et al.

[11] 4,341,609
[45] Jul. 27, 1982

[54] ELECTROCHEMICAL CONVERSION OF BIOMASS

[75] Inventors: Abolghassem Eskamani, Aurora; Helen D. Dernar, Parma, both of Ohio

[73] Assignee: The Standard Oil Company, Cleveland, Ohio

[21] Appl. No.: 238,307

[22] Filed: Feb. 26, 1981

[51] Int. Cl.$^3$ ............................................. D21C 3/22
[52] U.S. Cl. ..................................... 204/132; 204/131
[58] Field of Search .................... 204/72, 78, 131, 132

[56] References Cited

U.S. PATENT DOCUMENTS

| | | | |
|---|---|---|---|
| 616,988 | 1/1899 | Summers | 204/132 |
| 1,780,750 | 11/1930 | Horn | 204/132 |
| 2,828,253 | 3/1958 | Kurz | 204/132 |
| 4,075,071 | 2/1978 | Kirschbaum | 204/131 |
| 4,119,506 | 10/1978 | Bashforth | 204/131 |

*Primary Examiner*—R. L. Andrews
*Attorney, Agent, or Firm*—William A. Heidrich; Herbert D. Knudsen; Larry W. Evans

[57] ABSTRACT

A process for converting plant biomass to its constituent parts of lignin, cellulose and hemicellulose and further derivatives comprises treating the biomass in the anodic section of an electrochemical cell in the presence of an electrolyte solution. The rate of enzymatic cellulose hydrolysis of treated biomass is enhanced.

10 Claims, No Drawings

ELECTROCHEMICAL CONVERSION OF BIOMASS

BACKGROUND OF THE INVENTION

1. Field of the Invention

This invention relates to a process for the electrochemical treatment of plant biomass material to convert it into its constituent parts. More particularly, this invention relates to a process for converting lignocellulosic material into cellulose, hemicellulose and lignin.

2. Discussion of the Prior Art

Biomass, particularly agricultural byproducts and other plentiful sources of otherwise wasted lignocellulosic material, is being studied as a source of fuels, chemicals and polymers to supplement petroleum-derived materials. Because lignocellulose is a complex structure containing cellulose and hemicellulose bound with lignin, it must usually be treated and degraded in order to obtain more useful items.

Such useful items obtained from the processing of lignocellulose include organic acids such as acetic acid, lactic acid, butyric acid, malic acid, succinic acid, fumaric acid, citric acid and itaconic acid, and bipolymers including xanthan gum, pullulan, poly(hydroxybutyrates) and poly(alkonates). Other chemicals produced are solvents comprising ethanol, acetone, n-butanol, isopropanol and acetaldehyde, polyhydric alcohols such as propylene glycol, glycerol and butylene glycol in addition to specialty chemicals such as amino acids, enzymes and antibiotics.

Cellulose is a long-chain carbohydrate polymer composed of anhydroguclose units and has the empirical formula:

$$C_6H_{10}O_5$$

It is the major constituent of cell walls in higher plants, and is also found in lower plants such as mosses, ferns, algae and fungi. A dimer of cellulose, cellobiose, is formed during the conversion to sugars and will inhibit the degradation process.

Hemicellulose is a short-branched carbohydrate polymer occurring in the cell walls of plants in conjunction with cellulose and lignin. It is ordinarily extracted from plant materials with aqueous solutions of sodium hydroxide.

Lignin is a random-structured polymer formed from substituted phenylpropane units and is present in most plant materials. The proportion of lignin varies in different plant sources and in different parts of the same plant. One of its functions is to glue or cement the plant together. Although readily oxidized, it essentially cannot be hydrolyzed by acids. Lignin will also block the activity of cellulase, an enzyme which attacks the cellulose substrate. Lignin must usually be degraded or separated from the cellulosic portion of the biomass prior to significant hydrolysis of the cellulose.

While it may be conceptually simpler to hydrolyze the biomass directly, it is actually more efficient to first at least partially degrade or remove the lignin from the biomass before hydrolyzing the remaining cellulose or further processing the lignin. Hydrolysis of the cellulose substrates is the primary rate-limiting step in the conversion of biomass to useful fuels and chemicals. The rate of hydrolysis is in turn dependent upon the rate at which the biomass becomes exposed to the actions of acids or enzymes.

Several pretreatments are known to enhance the activity of these actions. The most common form of pretreatment is a physical destruction such as chipping, pulverizing, cutting or milling. This serves to alter the cellulose structure as well as expose more surface area of the lignocellulose. The benefits of a physical grinding as a pretreatment method are well known, and are shown for example in U.S. Pat. No. 2,801,955, a process for the extraction of hemicellulose, and U.S. Pat. No. 3,523,911, an acid-steam separation of lignocellulose. Pretreated material is more susceptible to enzyme action, acid hydrolysis or separation of the component parts by pulping, steam treatment, alkaline extraction, and the like.

After pulverization, the substrate typically undergoes a further separation or processing step. This can include acid or enzyme hydrolysis of the cellulose to produce simple sugars which can be fermented and distilled to alcohols. The lignin can be converted to dispersants or used as fillers, binders and resin extenders. Further processing of lignin can provide chemicals such as vanillin, methyl mercaptan and dimethyl sulfide. Hemicelluloses are often saccharified to produce sugars such as pentoses, and can have other uses in coating compositions, alcohols, xylose and xylitol, and the like. Such processing steps and techniques are more fully described in *Hydrolysis of Cellulose: Mechanisms of Enzymatic and Acid Hydrolysis* edited by R. D. Brown, Jr. and L. Jurasek, American Chemical Society, Washington, D.C., 1979.

SUMMARY OF THE INVENTION

The present invention is a process for converting biomass substrate into its constituent parts of cellulose, hemicellulose and lignin and further derivatives of these parts. The process comprises placing the substrate into the anodic section of an electrolytic cell containing an electrolyte and electrodes and applying an electromotive force sufficient to at least partially degrade the substrate.

DETAILED DESCRIPTION OF THE INVENTION

An electrochemical treatment of biomass has been found to degrade lignocellulosic material into its components and derivatives of the components. In particular, the rate of conversion of cellulose to simple fermentable sugars is enhanced. For the purposes of this invention, degradation shall mean both the separation of lignocellulose into its component parts of lignin, cellulose and hemicellulose as well as the further conversion of those parts to useful chemicals and materials. Degradation includes direct physical, chemical and structural changes in the lignocellulose as well as indirect alterations which result in enhanced further treatment by other known processes, such as enzyme or acid hydrolysis of cellulose.

Process Apparatus

The process is conducted in an electrochemical cell. Any size or shape of container which is designed for or capable of being adapted for use as an electrochemical cell can be used. Preferably, the cell is designed to provide easy handling of the biomass material and the electrolyte solution, and is optionally provided with a means for stirring or agitating the contents of the cell during the process.

A porous barrier must be provided to separate the cell into two sections. This barrier, typically positioned latitudinally between the sections, prevents the electrodes from making a short-circuit yet provides an ionic conducting path from one side of the cell to the other. It also prevents hydrogen and oxygen gases from mixing together inside the cell. Preferably, the barrier is selected from a material which is resistant to corrosion by the electrolyte in the presence of hydrogen or oxygen. A preferred barrier for use in this invention is sinterglass.

At least one electrode must be provided for each section of the cell. Almost any electronic conductor having a suitable catalytic service for the discharge of ions can be used. An electrode will advantageously have a large surface area to maximize the interface between the catalyst and the electrolyte solution. The specific size and shape will vary according to the design of the overall cell, although an electrode of 40 sq cm has been found to be suitable for a cell section having a volume capacity of about 70 ml of electrolyte. The electrode preferably has a means for detaching gas bubbles as they form in order to separate them from the electrolyte solution, but this is not essential. As is known in the art of electrolysis, the choice of material for the electrode also depends upon the choice of the electrolyte solution, because strong electrolyte solutions will corrode certain materials. Carbon and highly conductive metals such as platinum are especially suitable for use in this invention and are preferred.

Electrolyte

Any electrolyte which shows high ionic conductivity and has no detrimental effects on the process or the desired reaction product can be used. During the process, water is decomposed from the aqueous electrolyte solution into hydrogen and oxygen gas. The electrolyte must therefore not be volatile enough to be removed with the evolving gas and must not be chemically decomposed itself by the process. If the process is conducted for an extended period of time, additional water must be added to the system to replace water lost by decomposition.

Aqueous solutions of sulfuric acid and sodium hydroxide are preferred electrolytes. Other suitable electrolytes include ethylenediamine and ethylenediamine tetroacetic acid (EDTA).

Substrate

The biomass substrate can by any lignocellulosic material which is capable of being degraded in an electrolytic cell. Waste materials such as wood chips, corn leaves and stalks (corn stover) and the like are preferred for reasons of economy and convenience. Although not essential to the operation of the invention, the biomass is preferably cut and pulverized to smaller sizes in order to expose more of the lignocellulosic structure to the electrolyte. Alternatively, components of lignocellulose (e.g. pure cellulose, hemicellulose, or lignin) can serve as the substrate.

Process Conditions

The process can be conducted at any temperature between the freezing and boiling points of the electrolyte solution. Although the process proceeds more rapidly at higher temperatures, ambient or slightly higher temperatures are preferred for reasons of economy. Process temperatures between 20° and 35° C. are especially preferred.

Any suitable direct current power source may be connected to the electrolytic cell at the electrodes. As is the convention in electrolysis, the anode is the positive terminal of the cell. As is well known in the art, the potential needed to pass a current between the electrodes will vary with the distance between the electrodes and the conductivity of the electrolyte. The potential between the electrodes of smaller cells can vary from 5 to 50, preferably 10 to 30 and most preferably 10 to 15 volts. The current can range from 0.5 to 5, preferably 0.5 to 3 and most preferably about 1.5 amperes.

A device to agitate the contents of the electrolytic cell periodically or continuously during the process is preferably added in order to maximize contact between the substrate and the electrolyte. Suitable devices include magnetic stirrers, shearing blades, and pumps.

The time required for completion of the process will depend upon several factors including temperature, amount of substrate and electrolyte and electricity. At the conditions described in the examples, significant degradation occurred when the reaction had proceeded for 4–10 days. The effects of this degradation can be observed during the course of the electrochemical treatment by the change in appearance from a dark brown to a fluffy substrate. The process can be continued until extensive separation and degradation of the lignocellulose has occurred. Alternatively, the process can be operated for a shorter time as a pretreatment of lignocellulose which is then further treated by other known methods.

SPECIFIC EMBODIMENTS

Although the improvement achieved using the electrochemical treatment was visually apparent, it was not possible to directly measure the effect of the extent of the separation and degradation of lignocellulose. An indirect test was therefore devised in which the treated lignocellulose was subjected to enzymatic hydrolysis under controlled conditions. Lignocellulose which has been at least partially degraded has more sites exposed to enzyme activity. The amount of glucose produced by the enzyme hydrolysis was then determined and used as a measure of the effectiveness of the electrochemical treatment. Enzyme hydrolysis was also conducted on control groups which had not been treated with the electrochemical procedure.

In each of the following examples, the substrate was ground overnight in a ball mill to a fine powder. A measured amount of the substrate was placed in the anodic section of an electrochemical cell and treated at the specific conditions noted in the examples. This mixture was filtered and the liquid was analyzed for presence of glucose using a gas chromatograph. The solid filtrate was dried at 50° C. and autoclaved at 15 psi pressure and about 100° F. for about 15 minutes to sterilize the material and eliminate bacteria which might convert sugars to alcohols.

A cellulose/cellobiase enzyme system was used to convert the cellulose substrate to simple sugars, predominantly glucose. Dried and sterilized samples of the substrate combined with 100 ml distilled water. An enzyme mixture, usually 0.1 g cellulase and 0.1 g cellobiase, was then added. The samples were magnetically stirred and maintained in a closed system under a nitrogen atmosphere for at least one day. The enzyme hydrolysis was typically conducted at 50° C. and a pH of about 4–5.

The Worthington Statzyme® method (manufactured for Worthington Diagnostics, Division of Millipore Corp., Freehold, N.J.), a commercial photometric procedure for determining glucose levels in physiological fluids, was used to measure the effectiveness of the treatment. For this study, absorbance of the samples at 500 nm was measured and the amount of glucose present was determined by comparing those values to standard curves of absorbance versus mg glucose at 500 nm. In this technique, the change in absorbance at 500 nm was directly proportional to the glucose concentration in the sample. Unless otherwise noted, all of the examples followed the above procedures.

EXAMPLE 1

This example illustrates the kinetics of the enzymatic hydrolysis of treated biomass to glucose.

Approximately 30–50 g of corn leaves were placed in a ball mill and ground overnight to a fine powdery consistency, about 45 mesh. About 70 ml of an electrolyte solution, 10% sulfuric acid, was poured in both the anodic and cathodic sections of a glass electrolytic cell with a sinterglass barrier. About 0.35 g (dry weight) of the dark-brown pulverized substrate was added to the anodic section. Platinum electrodes were immersed in each side of the cell and about 1.0 amperes of current were provided at 10 volts.

The treatment proceeded for 7 days at room temperature (about 20°–25° C.) until the substrate had a light gray to white fluffy appearance. The substrate and solution were removed from the anodic section and neutralized with about 100 ml 20 N sodium hydroxide. The neutralized cell contents were filtered with a Millipore® filter apparatus with 5.0 micron paper, washed with distilled water, and the filtrate was then dried in a vacuum oven to prepare the substrate for enzymatic hydrolysis studies.

The dried substrate and the hydrolysis reaction vessel were then sterilized in an autoclave at 15 psi and 250° F. for 15 minutes. An enzyme system consisting of 0.02 g cellulase and 0.02 g cellobiase in 100 ml distilled water was added to 0.1 grams of the electrochemically treated biomass. This enzyme hydrolysis was conducted for 10 days at 50° C. and a pH of 5 under a nitrogen atmosphere. Results of the test for presence of glucose are shown in Table I below.

TABLE I

| Enzymatic Hydrolysis Kinetics | |
| --- | --- |
| Days | mg Glucose |
| 0 | 0.05 |
| 1 | 0.1 |
| 5 | 0.20 |
| 6 | 0.25 |
| 7 | 0.25 |
| 10 | 0.3 |

As shown above, the treated substrate produced some glucose (0.05 mg) shortly after beginning enzyme hydrolysis (at Day O). The amount of glucose formed increased over several days.

Comparison A

Because hydrolysis of cellulose with various acids is known in the art, it was necessary to determine that the effects of the electrochemical treatment were not merely due to the presence of the acidic electrolyte, sulfuric acid.

A cell system identical to that in Example 1 was prepared. Identical amounts of the substrate and sulfuric acid electrolyte were used, but no electric current was passed through the electrodes. The substrate had the original brown color and appearance after 7 days. No enzymatic hydrolysis test was conducted for Comparison A.

EXAMPLE 2

For this example, a commercial powdered cellulose (Solka-Floc®, made from purified wood pulp by Brown Company of Berlin, N.H.) was used as the substrate.

The cellulose was treated electrochemically for 4 days at the conditions noted in Example 1, then washed in distilled water and dried at 55° C. in a vacuum oven. Enzyme hydrolysis was conducted by adding 0.5 g cellulose substrate with 0.1 g cellulase and 0.1 g cellobiase in 100 ml sterilized distilled water. The hydrolysis was conducted at 50° C. in a pH of about 5 and produced the results shown below in Table III.

TABLE III

| Treated Pure Cellulose: Kinetic Study of Enzymatic Hydrolysis | |
| --- | --- |
| Days | Mg Glucose |
| ½ | 0.48 |
| 1 | 0.83 |
| 4 | 1.08 |
| 5 | 1.25 |
| 6 | 1.24 |
| 7 | 1.32 |
| 8 | 1.30 |

EXAMPLE 3

This experiment similar to Example 1, using 4.0 g corn leaves in 10% sulfuric acid. This system was treated for 10 days with 1 amp of current. Enzyme hydrolysis was conducted using 0.5 g treated substrate in 100 ml distilled water with 0.1 g cellulose and 0.1 g cellobiase, with other conditions as stated in Example 1. After one day, 0.28 mg of glucose were detected in the sample.

EXAMPLE 4

Corn leaves were again tested using 2.0 g ground corn leaves in the anodic section of an electrolytic cell with 10% sulfuric acid under the conditions of Example 3. After electrochemical treatment for about 3 weeks, enzymatic hydrolysis of the substrate produced about 0.25 mg glucose at the end of the first day.

Comparison B

Corn leaves were placed in 10% sulfuric acid for about 6 days, but no electricity was applied to the system. Enzymatic hydrolysis of a 0.5 g sample produced 0.20 mg glucose after the first day.

EXAMPLE 5

Example 3 was repeated using a Masterflex pump with tubing inserted in the anodic section of the cell to assist in circulation of the cell contents. The electrochemical treatment lasted 6 days. Results of the enzyme hydrolysis for the corn leaves electrochemically treated with improved agitation of cell contents is 1.0 mg glucose after 1 day.

Comparisons C, D and E

Other comparative experiments were done by placing biomass substrate in cells containing various concentrations of the electrolyte solution, but no electricity was applied.

About 2 g of corn leaves were placed in solutions of 10, 5 and 1% sulfuric acid identified respectively as Comparisons C, D and E. All ere magnetically stirred for 5 days and the mixture was then filtered with 5 micron filter paper and the substrate washed with distilled water, instead of the neutralization step of Example 1. After stirring had stopped, Comparison D stood for an additional 3 days before filtering, and Comparison E stood for 4 days. The recovered substrate was then dried in a vacuum oven at about 55° C., then sterilized in an autoclave for about 15 minutes at 15 psi and about 100° C. Enzyme hydrolysis produced the results shown in Table II.

TABLE II

| Electrolyte Without Electricity; Enzymatic Hydrolysis for One Day | | |
|---|---|---|
| Comparison | Solution | mg Glucose |
| C | 10% $H_2SO_4$ | 0.45 |
| D | 5% | 0.40 |
| E | 1% | 0.40 |

A comparison of the results between Example 5 and Comparisons B, C, and D, all of which have increased agitation of cell contents, shows that enzyme hydrolysis is more effective on electrochemically-treated corn stover.

EXAMPLE 6

Finely-pulverized hardwood sawdust which had been electrochemically treated by the method of this invention was subjected to enzyme hydrolysis as described in Example 1. After one day, 0.38 mg glucose was obtained.

Comparison F

Example 6 was repeated except that no electricity was applied to the system. After one day of enzyme hydrolysis, 0.20 mg glucose was detected.

Although only a few embodiments have been shown, it will be understood that many modifications can be made without departing from the scope of the present invention, which is to be limited only by the following claims.

We claim:

1. A process for degrading a substrate of lignocellulose or constituents of lignocellulose, the process comprising placing the substrate into the anodic section of an electrolytic cell containing electrodes and an electrolyte selected from the group consisting of sodium hydroxide and sulfuric acid, and applying an electromotive force of sufficient strength to at least partially degrade the substrate.

2. The process of claim 1 in which the substrate is selected from the group consisting of corn leaves, corn stover, cellulose, and wood sawdust.

3. The process of claim 1 in which the electrolyte is sulfuric acid.

4. The process of claim 3 in which the concentration of sulfuric acid is from about 1 to 10%.

5. The process of claim 4 in which the electromotive force has a voltage between about 5 to 50 volts DC.

6. The process of claim 5 in which the voltage is between 10 to 15 volts DC.

7. The process of claim 6 in which the current is from about 1.0 to 1.5 amperes.

8. The process of claim 7 in which the substrate consists of pulverized corn leaves.

9. A process for degrading corn stover into lignin, cellulose, hemicellulose and their derivatives, the process comprising placing pulverized stover into the anodic section of an electrolytic cell which contains a 10% solution of sulfuric acid and applying a direct current of about 1.5 amperes at about 10 volts.

10. In a process for converting lignocellulose to useful chemicals, the process characterized by pulverizing the lignocellulose, at least partially separating lignocellulose into its constituent parts of lignin, cellulose and hemicellulose, and further degrading these parts to form useful products, the improvement comprising placing the pulverized lignocellulose into the anodic section of an electrochemical cell containing an electrolyte selected from the group consisting of sodium hydroxide and sulfuric acid, and applying an electromotive force sufficient to at least partially degrade the lignocellulose.

* * * * *